United States Patent
Seeram et al.

(10) Patent No.: US 6,287,122 B1
(45) Date of Patent: Sep. 11, 2001

(54) FIBER-REINFORCED COMPOSITE PRODUCT WITH GRADED STIFFNESS

(75) Inventors: Ramakrishna Seeram; Ganesh Vijay Kumar; Teoh Swee Hin; Loh Poey Ling; Chew Chong Lin, all of Singapore (SG)

(73) Assignee: Institute of Materials Research & Engineering and National University of Singapore, Singapore (SG)

( * ) Notice: Subject to any disclaimer, the term of this patent is extended or adjusted under 35 U.S.C. 154(b) by 0 days.

(21) Appl. No.: 09/291,698

(22) Filed: Apr. 14, 1999

(30) Foreign Application Priority Data

Apr. 17, 1998 (SG) .................................... 9800874

(51) Int. Cl.$^7$ ...................................... A61C 5/08
(52) U.S. Cl. ............................ 433/220; 433/224
(58) Field of Search ................... 433/180, 215, 433/220, 221, 224, 225, 226

(56) References Cited

U.S. PATENT DOCUMENTS

| | | | |
|---|---|---|---|
| 2,472,483 | * | 6/1949 | Krippendorf . |
| 4,894,012 | * | 1/1990 | Goldberg et al. ................. 433/215 |
| 4,952,150 | * | 8/1990 | Schiwiora et al. ................. 433/220 |
| 5,037,404 | * | 8/1991 | Gold et al. . |
| 5,074,792 | * | 12/1991 | Bernadat ............................ 433/220 |
| 5,098,304 | * | 3/1992 | Scharf ................................ 433/215 |
| 5,251,640 | * | 10/1993 | Osborne . |
| 5,518,399 | * | 5/1996 | Sicurelli, Jr. et al. ............. 433/220 |
| 5,564,929 | * | 10/1996 | Alpert ................................ 433/224 |
| 5,797,748 | * | 8/1998 | Reynaud et al. .................. 433/224 |
| 5,816,816 | * | 10/1998 | Scharf ................................ 433/220 |
| 5,890,904 | * | 4/1999 | Reynaud et al. .................. 433/220 |
| 5,911,715 | * | 6/1999 | Berg et al. . |
| 5,915,970 | * | 6/1999 | Sicurelli, Jr. et al. ............. 433/220 |
| 5,919,044 | * | 7/1999 | Sicurelli, Jr. et al. ............. 433/220 |
| 5,989,032 | * | 11/1999 | Reynaud et al. .................. 433/224 |
| 6,012,924 | * | 1/2000 | Reynaud et al. .................. 433/220 |

* cited by examiner

*Primary Examiner*—Ralph A. Lewis
(74) *Attorney, Agent, or Firm*—Christie, Parker & Hale, LLP

(57) ABSTRACT

A fiber-reinforced composite material with graded stiffness, and method of making the same. The degree of stiffness variation may be controlled via modifications to the fabrication processes. Products with varying stiffness along their lengths are described. In one example, a dental post is fabricated from material according to the present invention which has one end with low stiffness adapted for insertion into the root of the tooth, and a high stiffness end suitable to support the restoration.

30 Claims, 5 Drawing Sheets

FIBER-REINFORCED COMPOSITE PRODUCT WITH GRADED STIFFNESS

FIELD OF THE INVENTION

The present invention is related to the fiber-reinforced composite materials. In particular, the present invention is related to a functionally graded fiber-reinforced composite material and processes for making the same. More particularly, this invention is related to a dental post and method of making the same.

BACKGROUND OF THE INVENTION

Dental posts are used in reconstruction of endodontically treated teeth. The function of the dental post is to provide retention and lateral stability to the restoration. The restorative material is used to build the core and the crown at the coronal end of the tooth. In order to provide effective lateral stability, the dental post should have high stiffness in the coronal region. Stiffness refers to Young's modulus, which is the resistance of a material to deformation. Another important function of the dental post is to disperse occlusal forces from the coronal region to the remaining tooth structure. In addition, a good dental post should have a long fatigue life and high corrosion resistance.

In view of the above-stated requirements, state-of-the-art dental posts are either made of stainless steel, titanium or other metal alloys, or fiber reinforced composites, which have stiffness much higher than that of dentine, Although, the high stiffness is generally recognized as being necessary for the effective support of the restorative material in the coronal region of the tooth in order to prevent loosening of core and crown, it also gives the major drawback of causing stress concentration at the apical end of the tooth. The rigid post stiffens the coronal posted section and shifts the flexure point apically. The effect of this stiffening is to cause the non-posted apical portion of the tooth to deform at the post apex, resulting in a stress increase in that portion of the canal wall. Furthermore, the cyclic loading and unloading during mastication requires consideration of fatigue failure. Since the maximum bending stresses occur in the vicinity of the apex of the post, any inclusions or defects within the wall of the dentine near the apical end of the post would create stress concentration that increases the risk of a fatigue crack formation. Defects and microfractures introduced during endodontic treatment and post access preparation could become areas contributing to stress concentration. As a result, fractures frequently occur at the root of the tooth. Furthermore, the high stress experienced at the post-dentine interface of a high stiffness post often causes loosening at the post-dentine interface.

Various designs have been suggested in the art to address some problems stated above. These include tapered posts (U.S. Pat. No. 5,104,321), and flexible posts (U.S. Pat. No. 5,518,399). For tapered posts, the change in the shape of the post affects the bending stiffness without changing the Young's modulus of the post. Since Young's modulus is a critical parameter in determining the stress loading at the post-dentine interface, a tapered post does not solve the problem of root stress resulting from the high stiffness of the post. Furthermore, wedging effect occurs at the tip of the tapered end, resulting in vertical fractures. A flexible post has a reduced Young's modulus, which reduces the problem of root stress, but may not give sufficient support to the restoration, resulting in loosening and early failure of the restoration.

OBJECT OF THE INVENTION

It is therefore an object of the present invention to provide a material for a dental post to overcome the shortcomings as stated above.

It is another object to provide a fiber-reinforced composite material with varying stiffness.

SUMMARY OF THE INVENTION

The present invention provides fiber-reinforced composite material with graded stiffness, and method of making the same. The degree of stiffness variation may be controlled via modifications to the fabrication processes. Products with varying stiffness along their lengths are described. In one example, a dental post is fabricated from material according to the present invention which has one end with low stiffness adapted for insertion into the root of the tooth, and a high stiffness end suitable to support the restoration.

DESCRIPTION OF THE INVENTION

An important parameter for excellent performance of the dental post is its stiffness. Since stress sharing within a system depends upon the material stiffness of each component, a key to the present invention is the recognition that the ideal dental post is one which gives graded material stiffness along its length. The post should reinforce the coronal region so as to reduce stress in the restoration and associated interfaces. In addition the post should not cause stress concentration at the apical end. This requires the post to take away the stresses from the coronal region and gradually unload them to the dentine. Therefore the segment of the post at the core region must be stiff to take away the stress from the core, while stiffness along the dentine region of the tooth should gradually be reduced to the value of the dentine. Hence, the post according to the present invention comprises segments of varying stiffness along its length. As fiber reinforced composite is used to make the dental post in the present invention, good fatigue and corrosion resistance is also achieved.

For the purpose of understanding the present invention, stiffness refers to Young's modulus. Segments of a post refers to imaginary divisions along the length of a single post for ease of description of graded stiffness, and do not necessarily mean an actual physical separation of the post into different sections. Braiding angle refers to the angle between a braided fiber and the longitudinal axis of a long product. The material may be any conventional composite material such as a combination of ceramic, polymer or metals. The materials may also be a combination of different polymer or different metals or different ceramic. The following are examples of methods of fabricating a post with graded stiffness.

For a dental post, the preferred stiffness at the apical end is approximately the same as the stiffness of the dentine i.e. 20 GPa. The stiffness at the coronal end is preferably much higher than the dentine stiffness, such as 100 GPa. The stiffness which can actually be achieved would depend on the material used. For example, a carbon fiber composite dental post may have a stiffness of 150–80 GPa at the coronal end, and 25–15 GPa at the apical end. Other stiffness ranges depends on the application, and may be obtained using the methods described below.

EXAMPLE 1

Figure 1A:
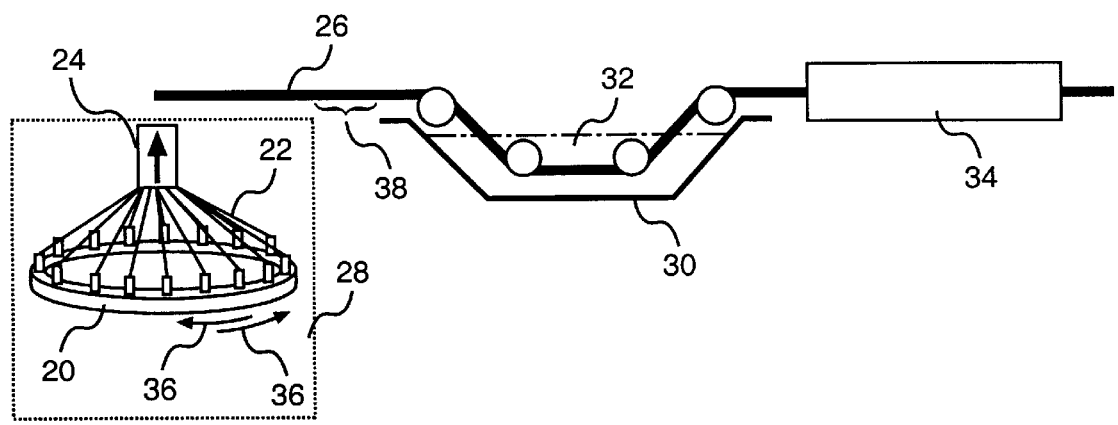
FIG. 1A is a schematic diagram to show one method of producing a post in accordance with the present invention.

Referring to FIG. 1A, spools 20 of metallic, ceramic or polymeric fibers 22 are interlaced into a preform 26 with or without a mandrel or core. After braiding in the braiding machine 28, the preform is transferred to a resin bath 30 containing unreacted resin 32. Once the unreacted resin has impregnated the fibers in the preform, it is transferred to a curing die 34 of the required diameter wherewith the resin is cured to form the polymeric component or matrix of the fiber-reinforced composite post. The polymeric component may be any kind of thermosetting resin such as epoxy, polyester, or molten or solvent dissolved thermoplastic resin.

Figure 1B:
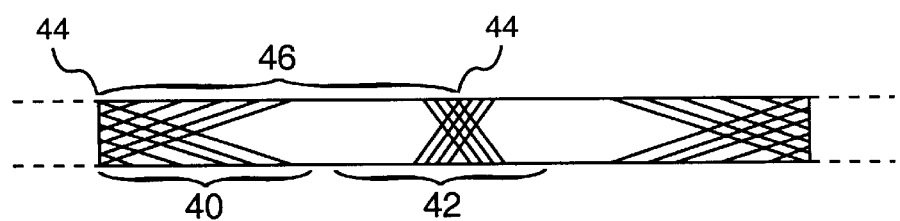
FIG. 1B is a diagram to show a preform produced according to the method shown in FIG. 1A.

According to the conventional method, the take-up speed N1 (shown by arrow 24) and spindle speed N2 (shown by arrow 36) has a fixed ratio and hence, the angle of braiding is fixed. According to the present invention, the ratio between the take-up speed N1 (24) and spindle speed N2 (36) is changed continuously in order to vary the angle of braiding. FIG. 1B is a schematic drawing of a preform made according to the present invention. This corresponds to section 38 in FIG. 1A. The angle of braiding in segment 40 with reference to the longitudinal axis of the post is smaller than the angle of braiding in segment 42. Since it is well known that the stiffness of the fiber-reinforced material is higher when the braiding angle is smaller, varying the take-up and spindle speed ratio would result in a product with varying stiffness. A dental post 46 in accordance with the present invention may then be obtained, for example, by cutting the material at sites 44. Hence post 46 would have one segment 40 which is of higher stiffness than segment 42. It should be understood that using this method, a continuous gradient of stiffness is obtained, and that describing the material as having different segments is merely to facilitate understanding of the inventive concepts.

EXAMPLE 2

Figure 2A:
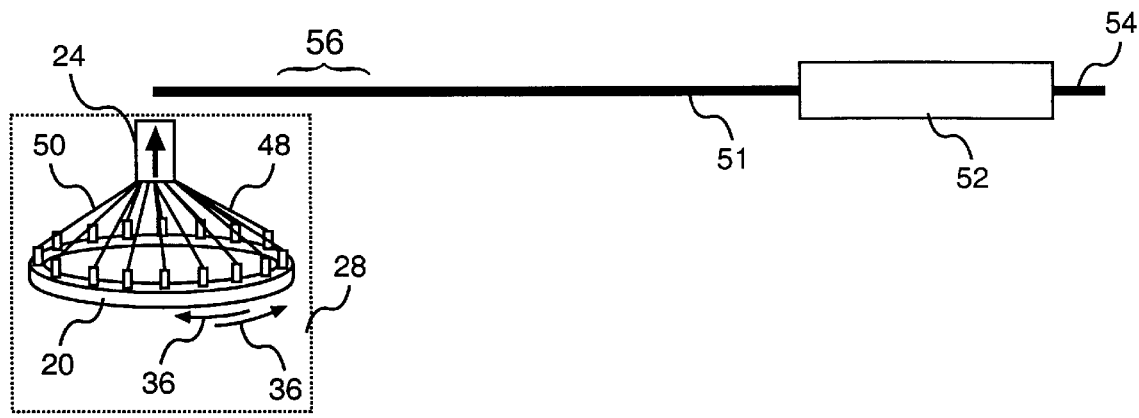
FIG. 2A is a schematic diagram to show a second method of producing a post in accordance with the present invention.
Figure 2B:
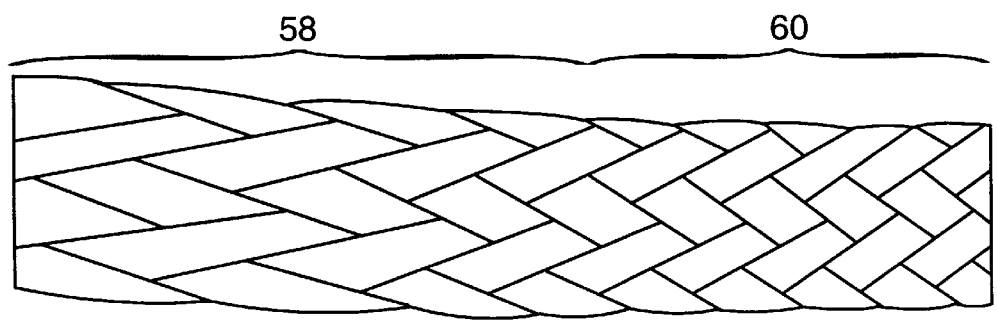
FIG. 2B is a photograph of a preform produced by the method shown in FIG. 2A.
Figure 3:
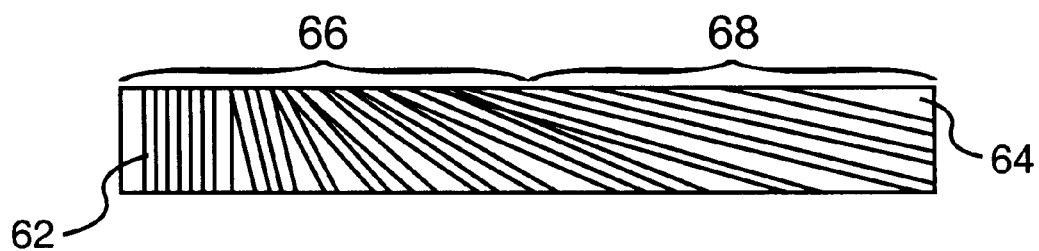
FIG. 3 is a schematic diagram to show a third method of producing a post in accordance with the present invention.

FIG. 2A shows a variation to the braiding method. In addition to the metallic, polymeric or ceramic reinforcement fibers 48, at least another set of the fibers is a polymeric material 50. During the braiding process, the ratio between the take-up speed N1 24 and spindle speed N2 36 is changed continuously in order to vary the braiding angle. The braided preform 51 is then transferred to mold 52 for compression molding at required temperature at which specific set of polymeric fibers melt and impregnate the reinforcement fibers. The final product 54 is one having varying stiffness along its length. Section 56 of the preform would have braided fibers similar to the ones shown in FIG. 1B, except those additional polymeric fibers are also intertwined. FIG. 2B shows a photograph of a preform dental post with a continual variation in the braid angles. Therefore, the stiffness in segment 58 is generally higher than the segment in section 60.

EXAMPLE 3

In a conventional filament winding method, a fiber or filament or tape 62 is wound around a core or mandrel 64. The filament may be made of metal, polymer or ceramic. The mandrel may be metal, ceramic or polymer. According to the present invention, the filament is wound at varying orientation with reference to the longitudinal axis of the core. A thermosetting matrix may also be provided according to conventional methods. The resultant product again has smaller angle and higher stiffness in segment 66, and larger angle and lower stiffness in segment 68.

EXAMPLE 4

Figure 4:
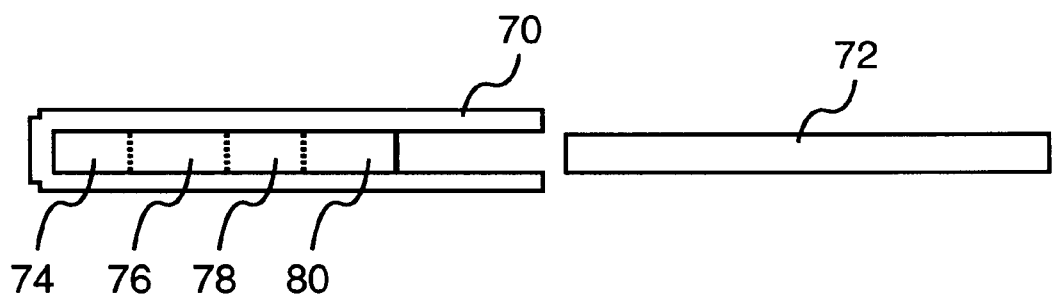
FIG. 4 is a schematic diagram to show a fourth method of producing a post in accordance with the present invention.

The stiffness of a composite fiber-reinforced post or long product may also be varied based on the fiber volume fraction. FIG. 4 shows a conventional casing 70 and plunger 72 for injection molding. In the conventional injection molding method, short fibers are mixed with a matrix material in a desired ratio and cured in the casing. In an embodiment of the present invention, mixtures with varying fiber volume fraction (i.e. varying proportions of fibers and matrix material) are transferred to the casing consecutively, and curing allowed to occur together. In the example shown in FIG. 4, four mixtures (74, 76, 78, 80) of varying fiber volume fractions are transferred to the casing. After curing, a single post is produced with four segments (74, 76, 78, 80) of varying proportions of fibers. Since it is well known that the stiffness of the product depends on the fiber volume fraction, the resulting product contains corresponding segments of varying stiffness. The fibers may be made of metal, silica, polymer or ceramic. The matrix material is again made from conventional material such as thermosetting resin or thermoplastic resin.

Test Results

Figure 5:
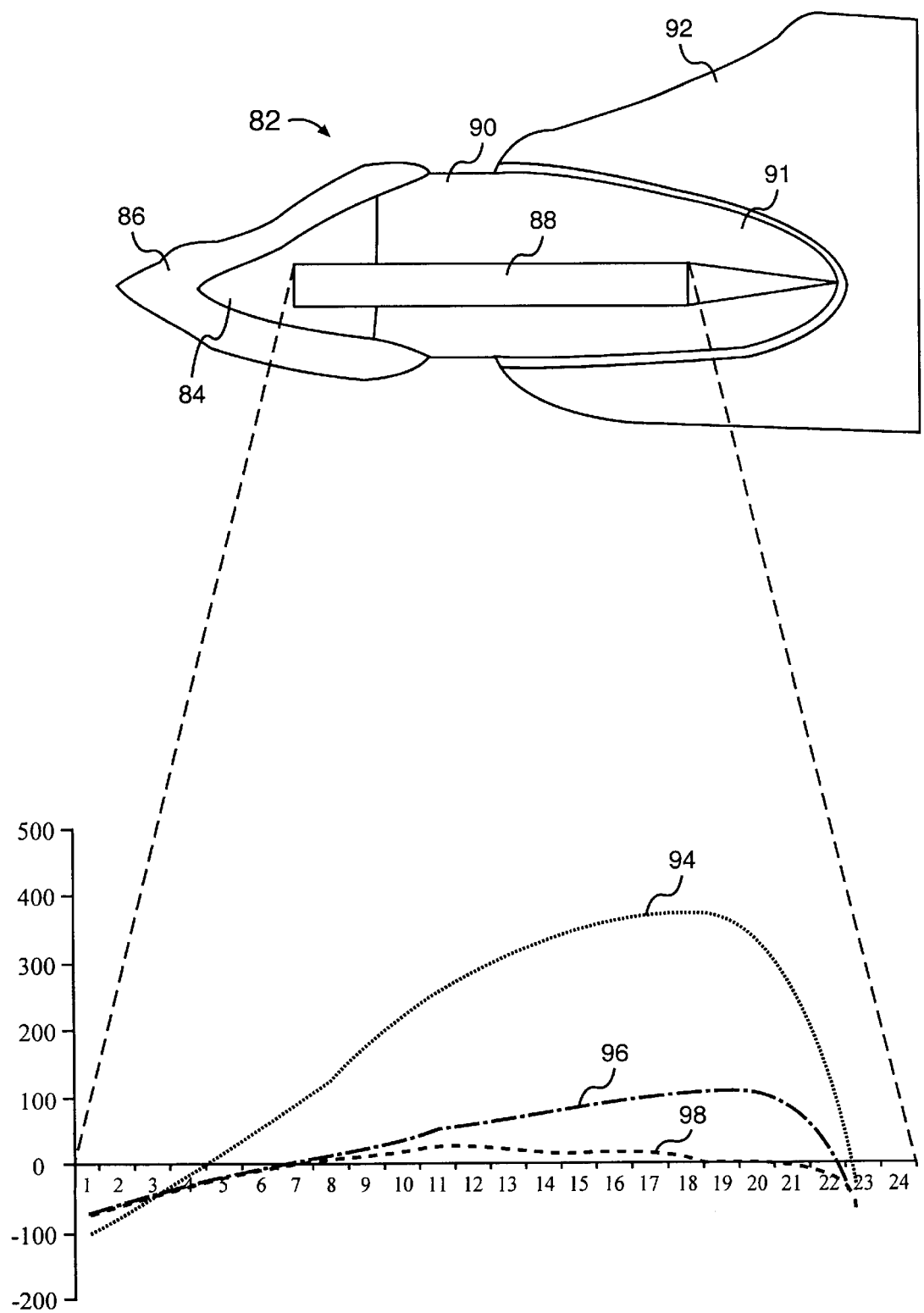
FIG. 5 is a finite element analysis showing normal tensile stress levels along post interface.
Figure 6:
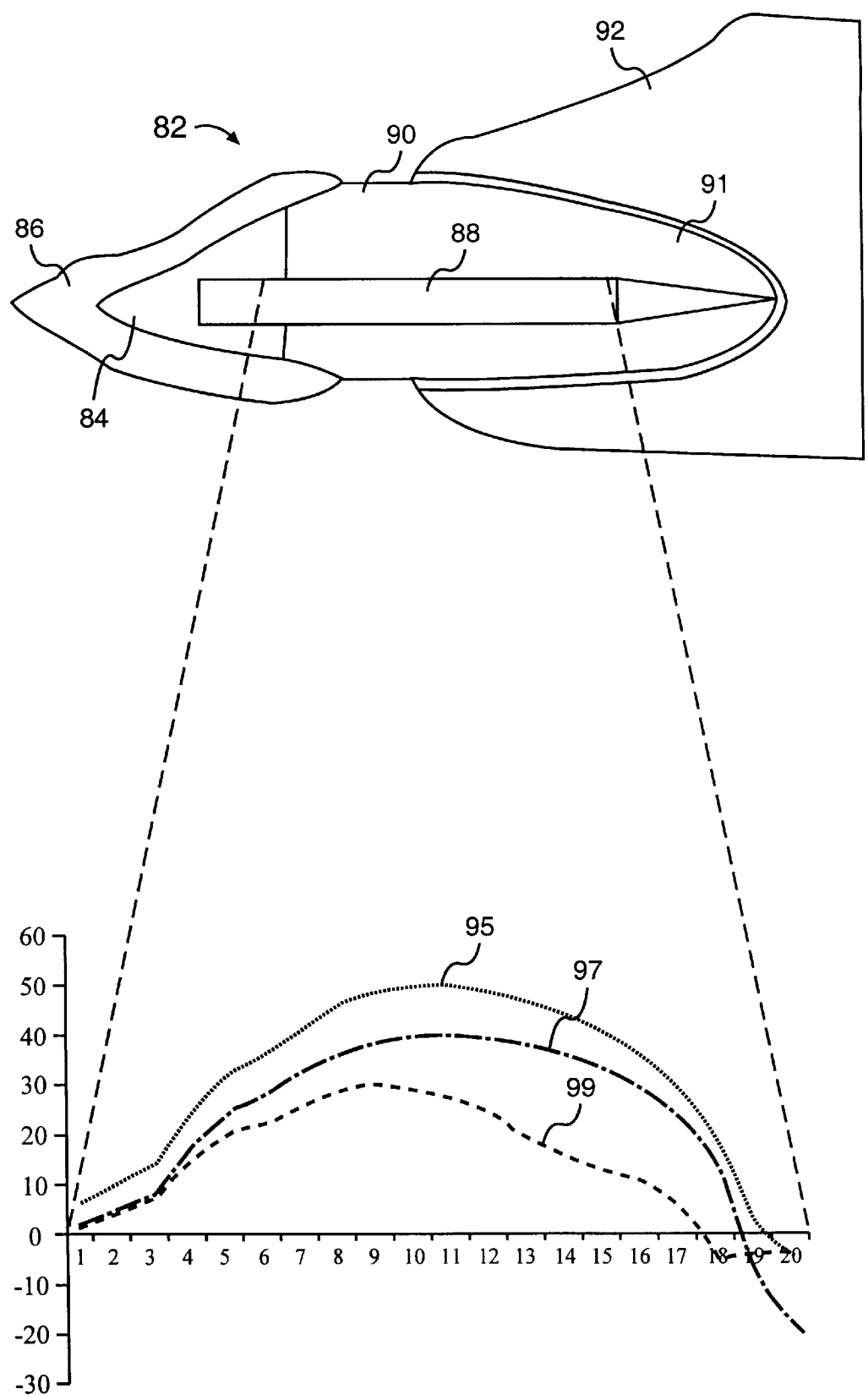
FIG. 6 is a finite element analysis showing normal tensile stress levels along dentine interface.

Dental posts with graded stiffness of 20 GPa to 80 GPa were compared with conventional posts using finite element stress analysis. The results of finite element analysis are shown in FIG. 5 and 6. A diagram of a restored tooth 82 is shown above the results to indicate the corresponding positions of the each test data at the horizontal axis. The restored core 84 and crown 86, the dental post 88, the dentine 90, the root 91, and the aveolar bone 92 are shown. The vertical axis shows the normal tensile stress levels in MPa.

FIG. 5 and 6 shows the tensile stress along the post and dentine respectively at the longitudinal interface. Curves 94 and 95 represents the stress levels for a conventional stainless steel or unidirectionally drawn carbon fiber post having high fiber volume fraction and 200 GPa stiffness. Curves 96 and 97 shows results for a uniform 80 Gpa carbon post. Curves 98 and 99 are results for a post with graded stiffness of 20 to 80 GPa in accordance with the present invention. For both post and dentine, the highest stress levels are detected for the conventional high stiffness post. The stress levels are reduced when the post stiffness is reduced to a uniform 80 GPa. The post with graded stiffness according to the present invention produces substantially lower stress levels than either of the uniform posts. The graded post shows a maximum of 25 MPa stress levels at the interface, which is only 7% of the 382 MPa peak stress experienced by the stainless steel post. At the dentine side of the interface, the peak stress level of 32 MPa detected using the graded post is only 61% compared to using the stainless steel post. These results are further summarized in Table 1 below.

TABLE 1

| Post Type | Stiffness | Highest stress level on Post at interface | Residual stress with reference to a 200 GPa post | Highest stress level on dentine at interface | Residual stress with reference to a 200 GPa post |
|---|---|---|---|---|---|
| Stainless steel or UD carbon | 200 GPa | 382 MPa | 100% | 52 MPa | 100% |
| UD Carbon | 80 GPa | 114 MPa | 30% | 42 MPa | 81% |
| Graded stiffness | 20–80 GPa | 25 MPa | 7% | 32 MPa | 61% |

While the present invention has been described particularly with reference to FIGS. 1 to 6 with emphasis on a dental post, it should be understood that the figures and the numerical values indicated are for illustration only and should not be taken as limitation on the invention. In addition it is clear that the graded fiber reinforced composite material and the methods of the present invention has utility in many applications, shapes and sizes where graded stiffness and function are required, such as sports equipment, structural elements, biomedical implants and devices etc. It is contemplated that other methods and numerous changes and modifications may be made by one of ordinary skill in the art without departing from the sprit and the scope of the invention described.

What is claimed is:

1. A pre-formed, non-tapered fiber-reinforced composition dental post with a plurality of segments, the first segment having a stiffness higher or lower than the stiffness of a neighboring segment, the dental post comprising interlaced fibers and a polymeric matrix, wherein interlacing angles of the fibers in the first segment are greater or smaller than interlacing angles of the fibers in the second segment.

2. A fiber-reinforced composite dental post according to claim 1 wherein the fiber is made from metal, polymer or ceramic.

3. A fiber-reinforced composite dental post according to claim 1 wherein the matrix component is made from metal, polymer or ceramic.

4. A fiber-reinforced composite dental post according to claim 1 wherein the fiber is a yarn impregnated with matrix wound around a mandrel, said composite post characterized in that the winding angle of said yarn in the first segment is higher or lower than the winding angle of a neighboring segment.

5. A fiber-reinforced composite dental post according to claim 4 wherein the yarn is a metal, polymer or a ceramic fiber.

6. A fiber-reinforced composite dental post according to claim 4 wherein the mandrel is made from metal, polymer or ceramic.

7. A fiber-reinforced composite dental post according to claim 4 wherein the matrix is made of thermosetting resin, or thermoplastic resin 8. A fiber-reinforced composite dental post according to claim 1 further comprising short fibers distributed within a matrix, said composite product characterized in that the fiber volume of the first segment is higher or lower than the fiber volume of a neighboring segment.

9. A fiber-reinforced composite dental post according to claim 8 wherein the short fibers are made from metal, polymer or ceramic.

10. A fiber-reinforced composite dental post according to claim 8 wherein the matrix is made of a thermosetting resin, or thermoplastic resin.

11. A fiber-reinforced composite dental post according to claim 1 wherein the dental post has a first segment, a last segment and at least one intermediate segment, said first segment having a stiffness of between 150 and 80 GPa and said last segment having a stiffness of between 25 and 15 GPa.

12. A method of making, prior to implantation in a patient, a pre-formed fiber-reinforced composite dental post, said dental post having a plurality of segments, said dental post further including a plurality of interlaced reinforcement fibers within a matrix, said method comprising the steps of:
   a) braiding said fibers at varying braiding angles prior to implantation in a patient to form a preform with a first segment with a higher or lower braiding angle than a neighboring segment; and
   b) curing said preform prior to implantation in a patient to form the fiber-reinforced composite dental post, wherein the different braiding angles create different degrees of flexibilities in the first and second segments.

13. A method of making a fiber-reinforced composite dental post according to claim 12 wherein an additonal step of impregnating the preform with unreacted resin is performed before curing.

14. A method of making a fiber-reinforced composite product according to claim 13 wherein said fiber is metallic, polymeric or ceramic.

15. A method of making a fiber-reinforced composite dental post according to claim 13 wherein said braiding angle is varied by varying the ratio between a take-up speed and a spindle speed in the braiding step.

16. A method of making a fiber-reinforced composite dental post according to claim 12 wherein said fiber is metallic, polymeric or ceramic.

17. A method of making a fiber-reinforced composite dental post according to claim 12 wherein the fibers contains at least one reinforcement fiber and one polymeric fiber, and said curing step is a compression molding step.

18. A method of making a fiber-reinforced composite dental post according to claim 17 wherein said reinforcement fiber is metallic, polymeric or ceramic.

19. A method of making a fiber-reinforced composite dental post according to claim 17 wherein said braiding angle is varied by varying a ratio between the take-up speed and a spindle speed in the braiding step.

20. A method of making a fiber-reinforced composite dental post according to claim 12 wherein said braiding angle is varied by varying the ratio between a take-up speed and a spindle speed in the braiding step.

21. A method of making a pre-formed fiber-reinforced composite dental post, said dental post having a plurality of segments, said dental post further including at least one wound filament within a matrix, said method comprising the step of winding said filament around a mandrel such that the winding angle of the filament in a first segment is bigger or smaller than the winding angle of the filament in a neighboring segment.

22. A method of making a fiber-reinforced composite dental post according to claim 21 wherein said mandrel is metallic, polymeric or ceramic.

23. A method of making a fiber-reinforced composite dental post according to claim 22 wherein said fiber is metallic, polymeric or ceramic.

24. A method of making a fiber-reinforced composite dental post according to claim 21 wherein said wound filament is further impregnated with a unreacted resin, followed by a curing step.

25. A method of making a fiber-reinforced composite dental post according to claim 24 wherein said fiber is metallic, polymeric or ceramic.

26. A method of making a fiber-reinforced composite dental post according to claim 21 wherein said fiber is metallic, polymeric or ceramic.

27. A method of making a pre-formed fiber-reinforced composite dental post with varying stiffness, said method comprising the steps of:
   a) mixing a first pre-determined proportion of fibers and matrix material and transferring to a casing;
   b) mixing a second pre-determined proportion of fibers and matrix material and transferring to the casing, said second pre-determined proportion having a higher or lower fiber volume fraction than said first pre-determined proportion;
   (c) sequentially adding additional varying fiber volume fractions to the casing; and
   (d) curing mixture (a) and mixture (b) and the varying fiber volume fractions (c) as one integral composite product such that the fiber volume fraction of the first pre-determined proportion and the second pre-determined proportion and the varying fiber volume fractions are substantially maintained and correspond to segments of the dental post.

28. A method of making a pre-formed fiber-reinforced composite dental post, said dental post having a plurality of segments, said dental post further including a plurality of interlaced reinforcement fibers and at least one polymeric fiber within a matrix, said method comprising the steps of:
   a) braiding said reinforcement fibers at varying braiding angles to form a preform with a first segment with a higher or lower braiding angle than a neighboring segment; and
   b) curing said preform in a compression molding step to form the fiber-reinforced composite dental post.

29. A method of making a pre-formed fiber-reinforced composite dental post, said dental post having a plurality of segments, said dental post further including a plurality of interlaced reinforcement fibers within a matrix, said method comprising the steps of:
   a) braiding said reinforcement fibers at varying braiding angles to form a preform with a first segment with a higher or lower braiding angle than a neighboring segment, wherein the braiding angle is varied by varying a ratio between a take-up speed and a spindle speed; and
   b) curing said preform to form the fiber-reinforced composite dental post.

30. A method of making a pre-formed fiber-reinforced composite dental post, said dental post having a plurality of segments, said dental post further including a plurality of interlaced reinforcement fibers within a matrix, the reinforcement fibers being selected from metallic, polymeric and ceramic fibers, said method comprising the steps of:
   a) braiding said reinforcement fibers at varying braiding angles to form a preform with a first segment with a higher or lower braiding angle than a neighboring segment; and
   b) curing said preform to form the fiber-reinforced composite dental post.

* * * * *